US00PP13269P2

(12) United States Plant Patent
Klemm

(10) Patent No.: US PP13,269 P2
(45) Date of Patent: Nov. 26, 2002

(54) GERANIUM PLANT NAMED 'KLEFEUER'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/036,933

(22) Filed: Dec. 31, 2001

(51) Int. Cl.[7] ..... A01H 5/00

(52) U.S. Cl. ..... Plt./330

(58) Field of Search ..... Plt./330

*Primary Examiner*—Kent L. Bell
(74) *Attorney, Agent, or Firm*—C. A. Whealy

(57) ABSTRACT

A new and distinct cultivar of Zonal Geranium plant named 'Klefeuer', characterized by its upright and uniform plant habit; freely branching and flowering habit; early flowering habit; and brilliant red-colored flowers arranged in rounded umbels held above the foliage on upright and strong peduncles.

1 Drawing Sheet

BOTANICAL CLASSIFICATION/CULTIVAR DESIGNATION

*Pelargonium×hortorum* cultivar 'Klefeuer'.

BACKGROUND OF THE INVENTION

The present invention relates to a new and distinct cultivar of Zonal Geranium plant, botanically known as *Pelargonium×hortorum*, and hereinafter referred to by the name 'Klefeuer'.

The new Zonal Geranium is a product of a planned breeding program conducted by the Inventor in Stuttgart, Germany. The objective of the breeding program was to develop new Zonal Geraniums with uniform plant habit, upright peduncles, and interesting flower and foliage colors.

The new Zonal Geranium originated from a cross-pollination made by the Inventor in 1997 of the *Pelargonium×hortorum* cultivar 'Klesatha', disclosed in U.S. Plant patent application Ser. No. 09/250,007, as the female, or seed, parent with a proprietary selection of *Pelargonium×hortorum* identified as ZN 104, not patented, as the male, or pollen, parent. The cultivar 'Klefeuer' was discovered and selected by the Inventor as a flowering plant within the progeny from this cross-pollination in a controlled environment in Stuttgart, Germany, in June, 1998.

Asexual reproduction of the new cultivar by terminal cuttings taken at Stuttgart, Germany since 1998 has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'Klefeuer'. These characteristics in combination distinguish 'Klefeuer' as a new cultivar and distinguish it from other known Zonal Geranium cultivars:

1. Upright and uniform plant habit.
2. Freely branching and flowering habit.
3. Early flowering habit.
4. Brilliant red-colored flowers arranged in rounded umbels held above the foliage on upright and strong peduncles.

Plants of the new Zonal Geranium differ primarily from plants of the female parent, the cultivar 'Klesatha', in the following characteristics:

1. Plants of the Zonal Geranium are more compact and not as vigorous as plants of the cultivar 'Klesatha'.
2. Plants of the new Zonal Geranium have more rounded umbels than plants of the cultivar 'Klesatha'.
3. Plants of the new Zonal Geranium have brilliant red-colored flowers whereas plants of the cultivar 'Klesatha' have orange red-colored flowers.

Plants of the new Zonal Geranium differ primarily from plants of the male parent, the selection ZN 104, in the following characteristics:

1. Leaves of plants of the new Zonal Geranium do not have a distinct zonation pattern whereas leaves of plants of the selection ZN 104 have a distinct zonation pattern.
2. Plants of the new Zonal Geranium have brilliant red-colored flowers whereas plants of the selection ZN 104 have deep red-colored flowers.

The new Zonal Geranium can be compared to plants of the cultivar 'Manepi', not patented. However, in side-by-side comparisons conducted in Stuttgart, Germany, plants of the new Zonal Geranium differed from plants of the cultivar 'Manepi' in the following characteristics:

1. Plants of the new Zonal Geranium were not as compact as plants of the cultivar 'Manepi'.
2. Plants of the new Zonal Geranium had more rounded umbels than plants of the cultivar 'Manepi'.
3. Plants of the new Zonal Geranium had brilliant red-colored flowers whereas plants of the cultivar 'Manepi' had orange red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of a typical flowering plant of 'Klefeuer' grown in a 12-cm container.

DETAILED BOTANICAL DESCRIPTION

Plants of the cultivar 'Klefeuer' have not been observed under all possible environmental conditions. The phenotype may vary somewhat with variations in environment, such as temperature and light intensity, without, however, any variance in genotype.

The aforementioned photograph, following observations, and averaged measurements describe plants that were planted in January in 12-cm pots in Stuttgart, Germany, and grown under commercial practice in a glass-covered greenhouse with day temperatures ranging from 18 to 22° C., night temperatures ranging from 15 to 18° C., and light levels ranging from 20,000 to 50,000 lux. The photograph and information for the detailed botanical description were taken about 15 weeks after planting rooted young plants.

In the following description, color references are made to The Royal Horticultural Society Colour Chart, 1995 Edition, except where general terms of ordinary dictionary significance are used.

Botanical classification: *Pelargonium×hortorum* cultivar 'Klefeuer'.

Parentage:

*Female parent.*—*Pelargonium×hortorum* cultivar 'Klesatha', disclosed in U.S. Plant patent application Ser. No. 09/250,007.

*Male parent.*—Proprietary selection of *Pelargonium×hortorum* identified as ZN 104, not patented.

Propagation:

*Type cutting.*—Terminal cuttings.

*Time to initiate roots.*—Summer: About 11 days at 22° C. Winter: About 14 days at 20° C.

*Time to produce a rooted young plant.*—Summer: About 18 days at 22° C. Winter: About 20 days at 20° C.

*Root description.*—Fine, freely branching, and white in color.

Plant description:

*General appearance.*—Upright and uniform plant habit; densely foliated.

*Crop time.*—About three months are required to produce a finished flowering plant in 12-cm container.

*Growth and branching habit.*—Moderately vigorous. Freely branching, about four or five lateral branches develop without pinching, that is, removal of terminal apices.

*Plant height* (*to top of flower umbels*).—About 20 cm.

*Plant height* (*to top of foliar plane*).—About 17.5 cm.

*Plant width.*—About 20 cm.

*Lateral branches.*—Length: About 7 cm. Internode length: About 1 cm. Texture: Slightly pubescent. Color: 139C.

*Foliage description.*—Arrangement: Alternate, simple. Quantity of leaves per lateral branch: About 6 or 7. Length: About 7 cm. Width: About 9 cm. Shape: Reniform. Apex: Rounded. Base: Lobed, not overlapping. Margin: Crenate. Venation pattern: Palmate. Texture: Upper surface: Slightly pubescent. Lower surface: Glabrous. Color: Young and fully expanded foliage, upper surface: 137B; no distinct zonation pattern. Young and fully expanded foliage, lower surface: 137C. Venation, upper and lower surfaces: 137D. Petiole: Length: About 5.5 cm. Diameter: About 4 mm. Color, upper and lower surfaces: 139C.

Flower description:

*Flower arrangement.*—Brilliant red-colored flowers arranged in rounded hemispherical umbels arising from apical leaf axils. Umbels displayed above the foliage on upright and strong peduncles. Flowers semi-double to double in form, rounded and cup-shaped. Umbels persistent, flowers not persistent. Flowers not fragrant.

*Quantity of flowers.*—Freely flowering habit; at full flower, plants have about 7 to 11 open and developing umbels with about 18 to 30 flowers and flower buds per umbel.

*Flowering season.*—Year-round under greenhouse conditions. In the garden, flowering is continuous from spring until fall.

*Time to flower.*—Early flowering; plants start flowering about 74 days after planting rooted young plants.

*Flower longevity.*—Flowers last about 5 to 10 days on the plant.

*Umbel size.*—Height: About 9 cm. Diameter: About 10 cm.

*Flower size.*—Diameter: About 4.5 cm. Depth (height): About 1.5 cm.

*Flower buds.*—Length: About 1 cm. Diameter: About 7 mm. Shape: Elliptic. Color: 184A to 184C.

*Petals.*—Quantity per flower: About 7 to 10. Length: About 2.5 cm. Width: About 2.1 cm. Shape: Ovate. Apex: Rounded. Base: Attenuate. Margin: Entire. Texture, upper and lower surfaces: Smooth, velvety. Color: When opening and fully opened, upper surface: 44B, towards base, 44C; color does not fade with subsequent development. When opening and fully opened, lower surface: 44C. Venation, upper and lower surfaces: 44B.

*Petaloids.*—Quantity per flower: About 2 to 6. Length: About 3 to 10 mm; irregular in size. Width: About 1 to 5 mm; irregular in size. Shape: Variable, irregular. Apex: Mostly rounded. Base: Attenuate. Margin: Mostly entire. Texture, upper and lower surfaces: Smooth, velvety. Color: When opening and fully opened, upper surface: 44B, towards base, 44C; color does not fade with subsequent development. When opening and fully opened, lower surface: 44C. Venation, upper and lower surfaces: 44B.

*Sepals.*—Quantity per flower: Five, arranged in a single whorl. Length: About 9 mm. Width: About 4 mm. Shape: Elliptic. Apex: Narrowly acute. Margin: Entire. Texture, upper and lower surfaces: Pubescent, velvety. Color, upper and lower surfaces: 139C.

*Peduncle* (*umbel stem*).—Length: About 12.5 cm. Diameter: About 5 mm. Angle: Erect. Strength: Strong. Texture: Slightly pubescent. Color: 139C.

*Pedicel* (*individual flower stem*).—Length: About 2.25 cm. Diameter: About 2 mm. Angle: Erect. Strength: Moderately strong. Texture: Slightly pubescent. Color: 139C overlain with 184A.

*Reproductive organs.*—Androecium: Anther quantity per flower: Five. Anther length: About 3 mm. Anther shape: Ovate. Anther color: 41A. Pollen amount:

Moderate. Pollen color: 40B. Gynoecium: Pistil quantity per flower: One. Pistil length: About 9 mm. Stigma shape: Five-parted, star-shaped. Stigma color: 57D. Style length: About 4 mm. Style color: 162D. Ovary color: 149D.

*Seed.*—Length: About 4.5 mm. Diameter: About 1.75 mm. Shape: Ovoid. Color: Brown.

Disease tolerance: Plants of the new Zonal Geranium have been observed to be somewhat tolerant to pathogens common to Pelargonium, such as Botrytis.

Weather tolerance: Plants of the new Zonal Geranium have been observed to tolerate rain, wind, and temperatures from about 8 to 30° C.

It is claimed:

1. A new and distinct cultivar of Zonal Geranium plant named 'Klefeuer', as herein illustrated and described.

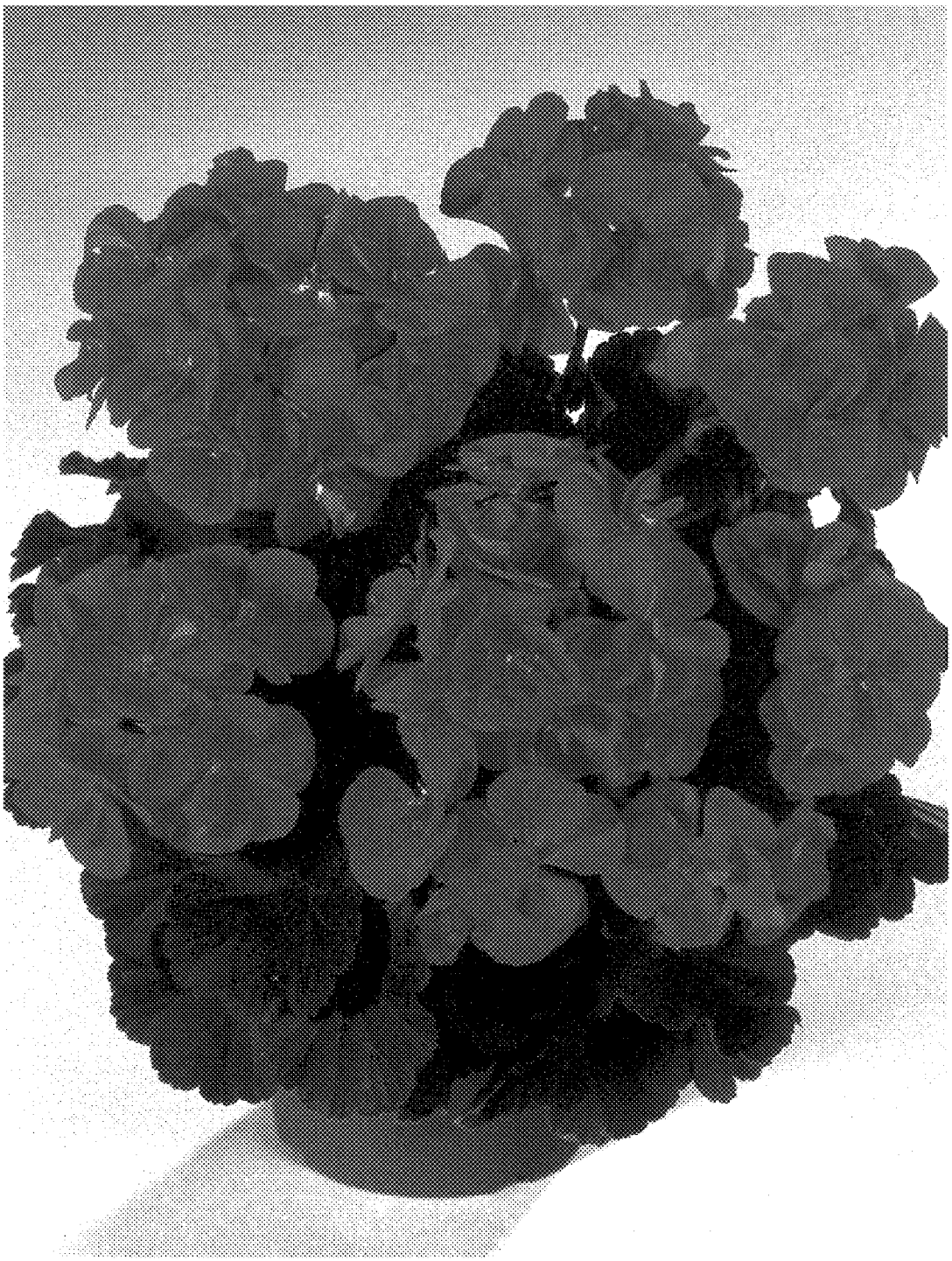

* * * * *